US010568945B2

(12) United States Patent
Lentsch et al.

(10) Patent No.: US 10,568,945 B2
(45) Date of Patent: Feb. 25, 2020

(54) COMPOSITIONS AND METHODS FOR INDUCING LIVER REGENERATION BY ADMINISTERING HEPATOCYTE-DERIVED EXOSOMES

(71) Applicant: University of Cincinnati, Cincinnati, OH (US)

(72) Inventors: Alex B. Lentsch, Hebron, KY (US); Michael J. Edwards, Cincinnati, OH (US); Erich Gulbins, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 808 days.

(21) Appl. No.: 14/696,531

(22) Filed: Apr. 27, 2015

(65) Prior Publication Data

US 2015/0306189 A1    Oct. 29, 2015

Related U.S. Application Data

(60) Provisional application No. 61/984,295, filed on Apr. 25, 2014.

(51) Int. Cl.
*A61K 38/50* (2006.01)
*A61K 38/45* (2006.01)
*A61K 31/164* (2006.01)
*A61K 9/00* (2006.01)

(52) U.S. Cl.
CPC ............ *A61K 38/50* (2013.01); *A61K 9/0019* (2013.01); *A61K 31/164* (2013.01); *A61K 38/45* (2013.01); *C12Y 207/01091* (2013.01); *C12Y 305/01023* (2013.01)

(58) Field of Classification Search
None
See application file for complete search history.

(56) References Cited

U.S. PATENT DOCUMENTS

| | | |
|---|---|---|
| 2011/0003008 A1 | 1/2011 | Lim |
| 2012/0093885 A1 | 4/2012 | Sahoo et al. |
| 2013/0143314 A1 | 6/2013 | Shiels et al. |

FOREIGN PATENT DOCUMENTS

WO    2014028493 A2    2/2014

OTHER PUBLICATIONS

Yeo et al. (Journal of Circulating Biomarkers, Nov 2013, pp. 1-12) (Year: 2013).*
Masyuk et al. (Journal of Hepatology, vol. 59, pp. 621-625, 2013) (Year: 2013).*
Attama, et al., Recent Advance in Novel Drug Carrier Systems, Chapter 5, "Lipid Nanoparticulate Drug Delivery Systems: A Revolution in Dosage Form Design and Development"; 2012, pp. 107-140.
Fan et al, Gene Therapy—Tools and Potential Applications, Chapter 5, "Polylipid Nano article, a Novel Lipid-Based Vector for Liver Gene Transfer"; 2013.
Fouraschen et al, "Secreted Factors of Human Liver-Derived Mesenchymal Stem Cells Promote Liver Regeneration Early After Partial Hepatectomy"; Stem Cells and Development; vol. 121, No. 13, 2012.
Lasser et al, "Isolation and Characterization of RNA-Containing Exosomes," J. Vis, Exp., e3037, 2012.
Thery et al, "Isolation and Characterization of Exosomes from Cell Culture Supernatants and Biological Fluids," Curr. Protoc. Cell Biol., Chapter 3, Unit 3, 22 (2006).

* cited by examiner

*Primary Examiner* — Meera Natarajan
(74) *Attorney, Agent, or Firm* — Dinsmore & Shohl LLP

(57) ABSTRACT

A pharmaceutical composition containing (1) a therapeutically effective amount of hepatocyte-derived exosomes; and (2) a pharmaceutically-acceptable carrier is provided. Also provided herein is a method of inducing liver regeneration in a patient in need thereof, the method including administering to the patient a therapeutic amount of hepatocyte-derived exosomes, wherein liver regeneration is induced. Methods for up-regulating synthesis of synthesis of sphingosine-1-phosphate (S1P) in a hepatocyte by contacting the hepatocyte with at least one vesicle containing sphingosine kinase 2, and, optionally, ceramide and neutral ceramidase, are also disclosed.

10 Claims, 5 Drawing Sheets

COMPOSITIONS AND METHODS FOR INDUCING LIVER REGENERATION BY ADMINISTERING HEPATOCYTE-DERIVED EXOSOMES

PRIORITY

This application claims priority to U.S. Provisional Application No. 61/984,295 having a filing date of Apr. 25, 2014, the entire disclosure of which is incorporated herein.

STATEMENT REGARDING FEDERALLY SPONSERED RESEARCH OR DEVELOPMENT

This invention was made with government support under DK 056029 awarded by National Institutes of Health. The government has certain rights in the invention.

FIELD OF THE INVENTION

The present disclosure relates to the field of therapeutic treatment of liver disorders. Specifically, the present disclosure relates to inducing liver regeneration in a patient via administration of hepatocyte-derived exosomes or reagents found in hepatocyte-derived exosomes.

BACKGROUND

Hepatic ischemia/reperfusion (I/R) is a major cause of liver injury and dysfunction after extended liver resection, liver transplantation or hemorrhagic shock. The process of liver repair and regeneration following hepatic I/R injury involves interactions between several cytokines and growth factors to stimulate hepatocyte proliferation and to restore liver mass. CXC chemokines are known to be important for these processes and previous work has demonstrated that the chemokine receptor, CXCR2, regulates liver recovery and regeneration after I/R injury. While several growth factors are known to be critical for liver regeneration, whether liver parenchymal cells can communicate with one another to promote regeneration is unknown.

Liver repair and regeneration after ischemia/reperfusion injury is of major clinical interest. The need persists to develop improved compositions and methods for repairing and regenerating the liver after liver injury.

SUMMARY

The present investigators discovered that exosomes trigger liver regeneration after ischemia/reperfusion (I/R) injury of the liver, and that exosomes induce a dose-dependent proliferation in hepatocytes in vitro and in vivo and mediate liver regeneration after I/R.

Accordingly, one embodiment of the invention is directed to a pharmaceutical composition comprising: a therapeutically effective amount of hepatocyte-derived exosomes; and a pharmaceutically-acceptable vehicle or carrier. Carriers/Vehicles may include water or saline or any vehicle suitable for stable containment and delivery with substantially retained bioactivity of the exosomes at the target site.

According to other embodiments, the pharmaceutical composition is formulated for targeted delivery to hepatocytes. The composition may comprise extracted exosomes, or the composition may comprises one or more active agents identified as reagents found in exosomes, for example ceramide, neutral ceramidase, and sphingosine kinase 2. The active agents may be encapsulated in a vesicle or stabilized, for example via emulsion and formulated as a lipid delivery system. The active agents may be delivered in the same or different compositions and dosing may concurrent or over extended time frames.

A further embodiment provides methods of treating liver injury and inducing liver regeneration in a patient in need thereof. The methods comprise administering to the patient a therapeutic amount of exosomes or reagents derived from exosomes, whereby liver regeneration is induced, and wherein a therapeutic amount is defined as an amount at least sufficient to result in a detectable increase in liver mass. Effectively-treated liver injuries may be associated with liver ischemia/reperfusion, liver transplantation, vascular surgery, traumatic injury, traumatic surgery, drug-induced acute liver injury, pathogen-induced acute liver injury, fibrosis of the liver, surgical resection of the liver, acute liver injury, or liver graft rejection after transplantation.

According to yet another embodiment, methods for up-regulating synthesis of sphingosine-1-phosphate (S1P) in a hepatocyte are provided. The methods comprise contacting the hepatocyte with at least one deliver and release vesicle containing sphingosine kinase 2, and, optionally, ceramide and neutral ceramidase. In specific embodiments, the vesicle surface comprises hepatocyte target antigen for targeted delivery to a hepatocyte.

These and other objects, features, embodiments, and advantages will become apparent to those of ordinary skill in the art by reference to the following Figures, Detailed description and the appended Claims.

DETAILED DESCRIPTION OF THE INVENTION

Figure 1:
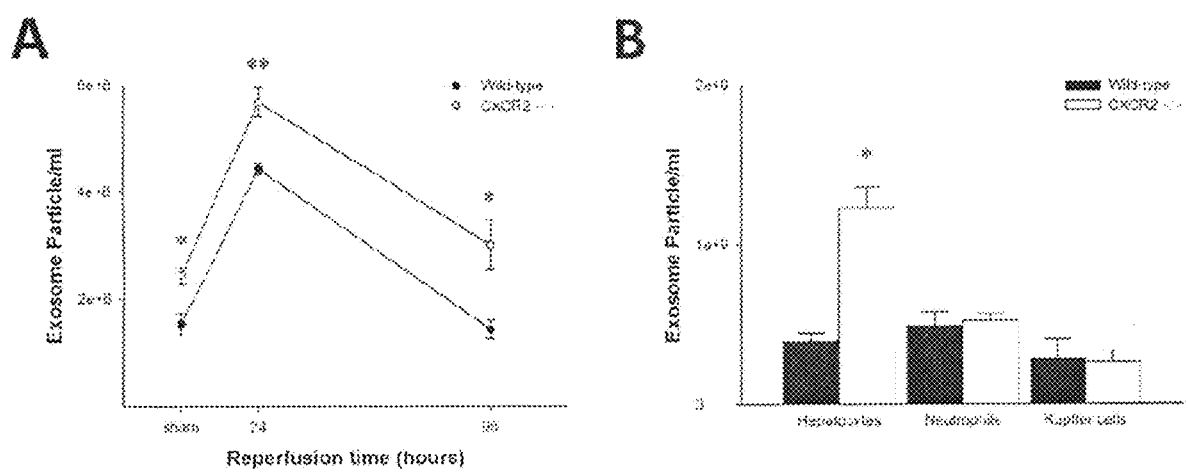
FIG. 1. Ischemia/reperfusion (IR) induces exosome release from hepatocytes. (A) I/R induces release of exosomes into the serum of wild-type and CXCR2-deficient mice. CXCR-2-deficient mice show higher exosome concentrations prior and after ischemia/reperfusion (I/R) injury. Serum exosome levels peak 24 hrs after reperfusion and normalize after 96 hours of reperfusion. (B) CXCR2-deficiency increased the formation and release of exosomes from cultured hepatocytes, but has no effect on the formation and the release of exosomes from ex vivo neutrophils, Kupffer cells, or liver sinusoidal endothelial cells. Data are mean±SEM with n=4-12 per group. *$P<0.05$ compared to wild-type mice. **$P<0.05$ compared to control and wild-type mice.

The details of one or more embodiments of the presently-disclosed subject matter are set forth in this document. Modifications to embodiments described in this document, and other embodiments, will be evident to those of ordinary skill in the art after a study of the information provided herein.

Unless defined otherwise, all technical and scientific terms used herein have the same meaning as commonly understood by one of ordinary skill in the art to which the subject matter belongs.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, pH, size, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

For the purposes of describing and defining the present disclosure it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

The present disclosure demonstrates that hepatocyte-derived exosomes contain the synthesis machinery to form S1P in hepatocytes that results in liver cell proliferation and organ regeneration after I/R injury. Exosomes are small membrane vesicles that are known to be involved in intercellular communication. Hepatocytes release exosomes, a process that is increased after I/R injury. Exosome-release from hepatocytes is controlled by the CXCR2-receptor that couples to neutral sphingomyelinase and ceramide. Hepatocyte proliferation is mediated by the transfer of neutral ceramidase and sphingosine-kinase in exosomes to hepatocytes resulting in the synthesis of sphingosine-1-phosphate (S1P) in target-hepatocytes. Inhibition of exosomal sphingosine-kinase prevents the proliferative effect of exosomes.

The role of exosomes as a mode of intercellular communication in this process was investigated. Exosomes are membrane nanovesicles (30-100 nm) that are released into the extracellular environment upon fusion of multivesicular bodies with the plasma membrane. Exosomes contain membrane components but also contain proteins, microRNAs and mRNAs. A variety of cell types, including hepatocytes, have the capacity to secrete exosomes into body fluids such as blood and urine. Previous studies have demonstrated that exosome release from cells depends on the activity of the neutral sphingomyelinase releasing ceramide from sphingomyelin and thereby controlling the process of exosome formation and release. An emerging interest on exosomes has been focused on intercellular communication via exosomes resulting in the delivery of exosomal content and modulation of cellular activities in recipient cells. This role in communication function of exosomes in liver regeneration was previously unknown.

The present investigators determined that hepatocyte-derived exosomes have the ability to initiate liver cell proliferation and regeneration. Results set forth in the Examples herein show that hepatocytes release exosomes after I/R in a process that is regulated by CXCR2, which controls neutral sphingomyelinase activity and cellular ceramide levels. Hepatocyte-derived exosomes contain neutral ceramidase and sphingosine kinase, deliver this cargo to injured hepatocytes, and induce proliferation via synthesis of sphingosine-1-phosphate (S1P). Exosomes are shown to mediate liver recovery and regeneration after I/R injury. Exosome release from hepatocytes is regulated by CXCR2, neutral sphingomyelinase and ceramide. CXCR2 appears to negatively regulate neutral sphingomyelinase and ceramide release. Deficiency of CXCR2 therefore results in a marked increase of exosome formation.

Described herein are novel compositions and methods for liver regeneration after injury or surgery. The data show that exosomes released by hepatocytes fuse with and promote the proliferation of hepatocytes, both in vitro and in vivo. The present disclosure defines the mechanism by which exosome production and release is regulated by the chemokine receptor, CXCR2, which appears to negatively regulate neutral sphingomyelinase activity and ceramide release within hepatocytes. While not desiring to be bound by theory, it is believed that the present disclosure describes the mechanism by which hepatocyte exosomes induce proliferation of hepatocytes. Namely, hepatocyte exosomes transfer the synthetic machinery to produce S1P and that intracellular generation of S1P is required for exosome-induced proliferation. Further, it is believed that the delivery of sphingosine kinase and neutral ceramidase mediates the observed proliferative and regenerative effects. Hence, a source of the exosomes may not be a limiting factor, such that exosomes derived from other sources similarly deliver therapeutic benefits. For example, exosomes derived from cultured mesenchymal stem cells may be used as the vehicle to deliver sphingosine kinase and neutral ceramidase to the targeted area.

Accordingly, one embodiment of the invention is directed to pharmaceutical compositions comprising a therapeutically effective amount of exosomes and a pharmaceutically-acceptable carrier/vehicle. In specific embodiments, the exosomes are derived from hepatocytes. A therapeutically effective amount is an amount effective to increase liver mass by an observable amount, for example by mass estimations via medical imaging or marker concentrations. A therapeutic amount may be delivered in a single dose, or in multiple doses across a treatment time frame. Suitable vehicle may be water or saline. The composition may comprise one or more substantially physiologically inert substances added to adjust a formulation to a desired consistency, to adjust pH, or to provide controlled, delayed or sustained release, depending on the desired route of administration. The pharmaceutical composition may be formulated for parenteral or enteral administration.

In some aspects the pharmaceutical composition is formulated for intravenous administration, for example as an injectable intravenous suspension or as an intravenous drip suspension. In other aspects the compositions may be formulated as injectable suspensions for administration directly into the peritoneal cavity through the abdominal wall, for example for delivery into peritoneal fluid surrounding at least a portion of the liver.

Non-limiting chemical techniques for solubizing water-insoluble drugs and biologics for oral and injectable administration include, for example, pH adjustment, cosolvents, complexation, microemulsions, self-emulsifying drug delivery systems, micelles, liposomes, emulsions, and combinations of these. In specific embodiments the pharmaceutical composition is formulated as an injectable suspension comprising a lipid delivery system. Lipid delivery systems are known in the art. Publications describing pharmaceutical lipid deliver systems and production thereof include, for example, "Recent Advance in Novel Drug Carrier Systems, Chapter 5 "Lipid Nanoparticulate Drug Delivery Systems: A Revolution in Dosage Form Design and Development 2012 Attama et al., p. 107-140; Q. Ashton Acton, PhD, Ed. "Drug Carriers—Advances in Research and Application" 2013 Edition, ScholarlyEditions™; and Fan and Wu, GeneTherapy—Tools and Potential Applications, Chapter 5 "Polylipid Nanoparticle, a Novel Lipid-Based Vector for Liver Gene Transfer" 2013; the entire disclosures of which are incorporated herein by this reference.

According to very specific embodiments, the pharmaceutical composition is formulated as a lipid delivery system comprising a stable oil-in-water emulsion of lipid layer-encapsulated droplets. In more specific embodiments, a target antigen for liver hepatocytes may be bound to the surface of a delivery particle for purposes of targeted delivery. In very specific embodiments the target antigen may be conjugated to a surface lipid via polymer such as PEG or a PEG derivative. In other specific embodiments the exosomes may be injected as formulations of vehicle such as a water or saline solution at therapeutic concentrations.

Other embodiments are directed to treatment of liver injury by administration of the pharmaceutical compositions. A treatable liver injury may be associated with one or more of liver ischemia/reperfusion, liver transplantation, vascular surgery, traumatic injury, traumatic surgery, drug-induced acute liver injury, pathogen-induced acute liver injury, surgical resection of the liver, acute liver injury, fibrosis of the liver, or liver graft rejection after transplantation. Pathogens may include for example, viruses, bacteria, fungi or parasites that are associated with liver damage. Drugs may include, for example, drugs administered for therapeutic purposes as well as drugs administered for social and/or recreational purposes. Dosing of exosomes or reagents will depend on the size, age, gender and overall health of the patient, as well as the extent of liver damage, and must be determined on a patient by patient basis. Dosing may be divided across a treatment time frame, and adjusted according to observed clinical result. In specific embodiments "treatment" comprises prophylactic treatment administered before, during, or directly after a medical procedure associated with liver damage, and in particular with liver I/R.

According to studies set forth in Examples 1, 4 and 5, the exosome components substantially responsible for therapeutic efficacy comprise ceramide, neutral ceramidase, and sphingosine kinase 2. In certain specific embodiments these components may be administered independent of other exosome components, and may be administered independently or in the same composition. The components may be encapsulated and the encapsulated components may be administered in a pharmaceutically acceptable carrier formulated for IV administration. In specific embodiments the composition may formulated for administration directly into the peritoneal cavity.

Embodiments directed to methods of inducing liver regeneration in a patient in need thereof are also provided.

The methods comprise administering to the patient a therapeutic amount of exosomes, whereby liver regeneration is induced, and wherein a therapeutic amount is defined as an amount at least sufficient to result in a detectable increase in liver mass. Exosomes may be derived from a healthy subject or from a subject suffering from hepatic ischemia or reperfusion injury. Without wishing to be bound by theory, the present investigators posit that exosomes are adapted by the body's response to liver injury and such adaptation is designed to promote liver regeneration. Exosomes extracted from a subject having experienced liver injury are therefore particularly suited for extraction and administration to a patient having experienced liver injury. Exosomes may be isolated from a body fluid, for example blood, lymph and peritoneal fluid. According to specific examples, the exosomes are isolated from serum from the subject. In very specific examples, the exosomes are isolated from a primary hepatocyte of the subject.

In some embodiments, liver regeneration is induced by treatment of a patient with pharmaceutical compositions comprising exosomes derived from a primary hepatocyte. In other embodiments liver regeneration is induced by treatment of a patient with one or more reagents that up-regulate synthesis of sphingosine-1-phosphate (S1P). Reagents are selected from sphingosine kinase 2, ceramide, neutral ceramidase, and combinations thereof. In a specific method, the one or more reagents are contained on or in a liposome-based vesicle and the vesicle may further comprise hepatocyte target ligand conjugated thereto. Reagents may also be administered directly into the peritneal cavity, for example, as a lipid emulsion.

EXAMPLES

The following examples are given by way of illustration and are in no way intended to limit the scope of the present invention.

Example 1

Materials and Methods

Hepatic I/R injury model

Male wild-type (BALB/c) and CXCR2-deficient mice on a BALB/c background were employed (Jackson Laboratory, Bar Harbor, Me.), weighing 22-28 g. The animals underwent either sham surgery or I/R. To induce partial hepatic ischemia mice were anesthetized with sodium pentobarbital (60 mg/kg, i.p.), a midline laparotomy was performed and an atraumatic clip was used to interrupt blood supply to the left lateral and median lobes of the liver. After 90 min of partial hepatic ischemia, the clip was removed to initiate hepatic reperfusion. Sham control mice underwent the same control without vascular occlusion. As indicated wild-type mice were injected intravenously with exosomes or saline (vehicle control) 24 and 48 hrs after reperfusion. Mice were sacrificed after the indicated periods of reperfusion, and blood and liver samples were taken for analysis.

Blood and Tissue Analysis

Blood was obtained by intracardiac puncture at time of sacrifice. For histologic analysis, tissue samples were fixed in 10% neutral-buffered formalin (Richard Allen Scientific, Kalamazoo, Mich.), processed, and embedded in paraffin before staining with hematoxylin and eosin (H&E).

Hepatocyte and Kupffer Cell Isolation

Hepatocytes were isolated from male wild-type or CXCR2-deficient mice by non-recirculating collagenase perfusion through the portal vein. Livers were perfused in situ with 45 mL Gibco Liver Perfusion Media (Invitrogen, Carlsbad, Calif.) followed by 45 mL of Gibco Liver Digestion Media (Invitrogen). The liver was excised, minced, and strained through a steel mesh. The dispersed hepatocytes were collected by centrifugation at 50×g for 2 min at 4° C. and washed twice with Williams media (Invitrogen) with 5% exosome-removed FBS (System Biosciences, California, CA). Hepatocytes were isolated by way of Percoll separation and washed twice with Williams media with 5% exosome-removed FBS.

The final pellet was resuspended in Williams media with 5% exosome-removed FBS. Hepatocytes were counted and viability was checked by Trypan blue exclusion. Kupffer cells were contained in the supernatants from the above wash. Cells were pelleted by centrifugation at 500×g for 9 min, resuspended in sterile $Ca^{2+}$- and $Mg^{2+}$-free Hank's buffered salt solution (HBSS) (pH 7.4), and subjected to fractionation by elutriation. Centrifugal elutriation was performed using a Beckman Coulter J20-XPI centrifuge with a JE 5.0 elutriator rotor at a constant speed of 3,200 rpm with stepwise increases in perfusion rates. Kupffer cells were collected at the 44 mL/min fraction. The resulting cell isolates were washed and viability was checked by Trypan blue exclusion.

To determine cell production of exosomes, hepatocytes or Kupffer cells were distributed onto 50-mm dish at a concentration of $2\times10^6$ cells/5 mL per dish and incubated overnight to allow cell adherence. The cells were re-incubated for 24 hrs and the culture media was collected.

Neutrophil Isolation

Neutrophils were isolated from the bone marrow of male wild-type or CXCR2-deficient mice. To this end, the femur and tibia were taken from the lower extremities. The bone marrow was then flushed with 10 ml HBSS using a 25-gauge needle and a 10 cc syringe. The bone marrow solution was centrifuged at 400×g for 5 min and the pellet was then resuspended in 0.2% NaCl followed by addition of 20 ml of 1.6% NaCl. The samples were filtered through a 70 μm filter and centrifuged at 400×g for 5 min, the pellet was resuspended in 5 ml HBSS. Neutrophils were isolated by way of Percoll separation and washed twice with HBSS solution. The final pellet was resuspended with RPMI media with 5% exosome-removed FBS. To determine cell production of exosomes, neutrophils were distributed onto a 50-mm dish at a concentration of $2\times10^6$ cells/5 mL per dish, incubated overnight, and the culture medium was collected.

Exosome Isolation

Exosomes were purified from serum and the culture media. Serum exosomes were isolated according to the manufacturer's protocol (System Biosciences). Briefly, 125 μL of serum was collected and mixed with Exoquick exosome precipitation (System Biosciences). Samples were centrifuged at 1500×g for 30 min, followed by incubation at 4° C. for 30 min. The supernatant was decanted and the exosome pellet was resuspended in phosphate-buffered saline (PBS). Exosomes were isolated using differential centrifugation as previously described (Lasser, et al., *Isolation and characterization of RNA-containing exosomes, J. Vis. Exp.*, e3037; Thery, et al., *Isolation and characterization of exosomes from cell culture supernatants and biological fluids, Curr. Protoc. Cell Biol.*, Chapter 3, Unit 3 22 (2006)). To isolate exosomes from cultured cells, the cells were incubated in Williams media supplemented with 5% exosome-removed FBS (System Biosciences) for 24 hrs, the culture media was collected and centrifuged at 300×g for 10 min. The supernatant was collected and centrifuged at 16,500×g for 20 min. The supernatant was then passed through a 0.22 μm filter and exosomes were harvested by 2-times centrifugation at 100,000×g for 70 min. The final pellet was resuspended in 100 ml PBS. The size of exosomes in the serum and the culture medium was determined using a Zetasizer Nano (Malvern Instruments, Malvern, UK) and the number of exosomes was assessed by the CD81-antigen ELISA kit (System Biosciences).

Ceramide Immunostaining

Hepatocytes were permeabilized by a 5 min incubation with 0.05% Triton X-100 (Sigma). Samples were washed and stained with anti-ceramide antibodies (1:100 dilution, Glycobiotech) at 4° C. for 45 min, followed by staining with Cy3-coupled secondary antibodies to mouse IgM (Jackson ImmunoResearch). Ceramide staining was analyzed by fluorescence microscopy.

Neutral Sphingomyelinase Activity

Neutral sphingomyelinase activity was measured as described previously. Primary hepatocytes were washed three times with PBS and lysed in 100 mM Tris-HCl (pH 7.4), 5 mM $MgCl_2$, 2.5 mM DTT, 0.2% Triton, 10 μg/ml each of aprotinin and leupeptin and immediately scraped off from the plate. The lysate was centrifuged for 10 min at 1,000×g and sonicated for 10 min in a bath sonicator. The supernatant was centrifuged for 60 min at 100,000×g. The resulting pellet (membrane fraction) was resuspended in the same buffer as above and incubated with 0.05 μCi per sample [$^{14}$C]sphingomyelin for 60 min at 37° C. to determine neutral sphingomyelinase activity. The substrate was dried prior to analysis, resuspended in the assay buffer, sonicated for 10 min and an aliquot was added to the samples. The reaction was stopped by the addition of 800 μL chloroform/methanol (2:1, v/v), phases were separated and radioactivity in the aqueous phase was measured by using liquid scintillation counting to determine the release of [$^{14}$C]phosphorylcholine from [$^{14}$C]sphingomyelin as a measure of sphingomyelinase activity.

Measurement of Ceramide by DAG-Kinase Method

Samples were extracted in 200 μl $H_2O$ and extracted in $CHCl_3$:$CH_3OH$:1N HCl (100:100:1, v/v/v). The lower phase was collected, dried, resuspended in 20 μl of a detergent solution (7.5% (w/v) n-octylglucopyranoside, 5 mM cardiolipin in 1 mM diethylenetriaminepentaacetic acid), sonicated for 10 min and 70 μl of a reaction mixture containing 10 μl diacylglycerol kinase (GE Healthcare Europe, München, Germany), 0.1 M imidazole/HCl (pH 6.6), 0.2 mM diethylenetriaminepentaacetic acid (pH 6.6), 70 mM NaCl, 17 mM $MgCl_2$ and 1.4 mM EGTA, 2 mM DTT, 1 μM ATP and 10 μCi [$^{32}$P]ATP were added. The kinase reaction was performed for 30 min at room temperature and terminated by addition of 1 ml $CHCl_3$:$CH_3OH$:1N HCl (100:100:1, v/v/v), 170 μl buffered saline solution (135 mM NaCl, 1.5 mM $CaCl_2$, 0.5 mM $MgCl_2$, 5.6 mM glucose, 10 mM HEPES, pH 7.2) and 30 μl of a 100 mM EDTA-solution. The lower phase was collected, dried and separated on Silica G60 TLC plates employing chloroform/acetone/methanol/acetic acid/$H_2O$ (50:20:15:10:5, v/v/v/v/v). Ceramide amounts were determined by comparison with a standard curve using C16 and C24 ceramides as substrates and analysis with a phospho-imager.

Measurement of S1P by ELISA

Quantification of S1P on hepatocytes was performed using a S1P ELISA kit (Echelon Biosciences) by following the instructions of the vendor.

Hepatocyte Proliferation

Hepatocytes were treated with hepatocyte-derived exosomes for 24 hrs. DNA incorporation of 5-bromo-20-deoxyuridine (BrdU) was employed to evaluate hepatocyte proliferation by exosomes, and data were normalized by the amount of viable cells and expressed as a ratio compared with medium alone. A commercial BrdU cell proliferation ELISA system (Abcam, Cambridge, UK) was used for this assay.

Proliferating Cell Nuclear Antigen Staining

Immunohistochemical (IHC) staining for proliferating cell nuclear antigen (PCNA) was performed on paraffin-embedded liver tissue with anti-PCNA antibody using a Dako ARK Peroxidase kit (Dako, Copenhagen, Denmark). According to the manufacturer's instructions, briefly, antigen retrieval was performed using citrate buffer (PH 6.0) and samples were stained with a biotinylated PC-10 monoclonal antibody (dilution of 1:50, Santa Cruz Biotechnology, Santa Cruz, Calif.) for 15 min at room temperature followed by 15 min incubation with streptavidin-peroxidase. Staining is completed by 5 min incubation with 3,3'-diaminobenzidine (DAB)+substrate-chromogen which results in a brown-colored precipitate at the antigen site. Sections were counterstained with hematoxylin. Evaluation of PC-10 immunostaining was performed based on the percentage of positive nuclei of 400-600 hepatocytes from four to six positive fields at high power (×400) and was expressed as the PCNA labeling index.

Exosome-hepatocyte Fusion

Exosomes were labeled with 2 μM PKH67 (Sigma-Aldrich) for 5 min, washed and incubated for 24 hours with cultured hepatocytes. The samples were washed and analyzed by fluorescence microscopy.

Statistical Analysis

Data are expressed as the mean± standard deviation (SD). Data were analyzed with a one-way analysis of variance, with a subsequent Student t test, or if indicated by ANOVA. Differences were considered significant when $P<0.05$.

Example 2

Hepatocytes Produce Exosomes, a Process that is Stimulated by Ischemia/Reperfusion To test whether I/R injury results in a release of exosomes in vivo, the number of exosomes in serum before and after liver I/R was measured. Exosomes were present in the serum of untreated mice and increased after I/R with maximum levels 24 hrs after reperfusion and normalization to baseline levels 96 hrs after reperfusion (FIG. 1A). To define molecular mechanisms that mediate the release of exosomes, CXCR2 (which has been previously shown to be critically involved in liver regeneration) was tested for its ability to regulate exosome release. Surprisingly CXCR2-deficient mice released higher numbers of exosomes into the serum than wild-type controls after I/R, even prior to any treatment (FIG. 1A).

Next, the number of exosomes released from hepatocytes, Kupffer cells and neutrophils, which are known to be critical for liver repair after I/R injury, was assessed. However, significant differences between the release of exosomes from any of the cell types was not detected (FIG. 1b). In contrast, only CXCR2-deficient hepatocytes produced more exosomes compared to their wild-type controls, while the release of exosomes did not differ between CXCR2-deficient and wildtype Kupffer cells or neutrophils (FIG. 1B). These data suggest that CXCR2 regulates the release of exosomes by hepatocytes.

Example 3

Regulation of Exosome Release from Hepatocytes by CXCR2 Occurs Through the Neutral Sphingomyelinase To identify the mechanism by which CXCR2 controls exosome release, the activity of the neutral sphingomyelinase and ceramide concentrations in wild-type and CXCR2-deficient hepatocytes was analyzed. Neutral sphingomyelinase and ceramide were recently shown to be key regulators of exosome formation.

Figure 2:
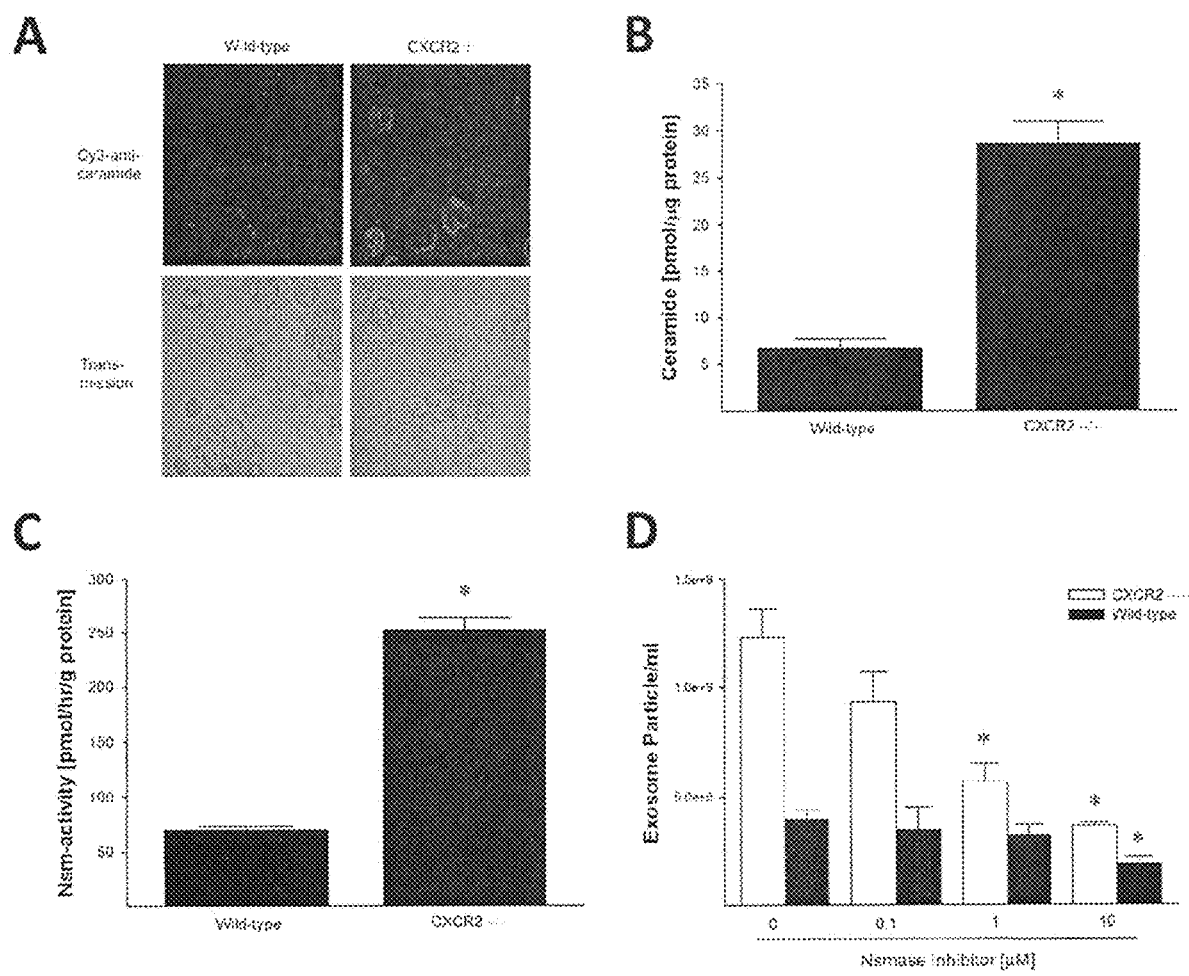
FIG. 2. CXCR2 regulates the neutral sphingomyelinase/ceramide system to release exosomes. (A) CXCR2-deficient cells show higher concentrations of ceramide than wildtype hepatocytes as determined by staining of isolated hepatocytes with Cy3-coupled anti-ceramide antibodies (A, upper panel). The intensity of the fluorescence staining in panel a reflects ceramide levels. The lower panel shows the light transmission picture. Data are representative for 4 similar stainings. (B) Ceramide activity in hepatocytes was determined by a ceramide kinase assay. Data are mean±SEM with n=4 per group. *$P<0.05$ compared to wild-type mice. (C) Neutral sphingomyelinase activity is increased in CXCR2-deficient hepatocytes compared to wild-type mice. Data are mean±SEM with n=4 per group. *$P<0.05$ compared to wild-type mice. (D) Release of exosomes from isolated wildtype and CXCR2-deficient hepatocytes is dose dependently blocked by pre-incubation the cells with the neutral sphingomyelinase inhibitor GW4869. Cells were treated with GW4869 for 48 hrs in Williams media supplemented with exosome-depleted FBS and the number of exosomes was determined using differential centrifugation and detection of exosomes using a CD81 antigen ELISA kit. Data are mean±SEM with n=4 per group, *P<0.05 compared to wild-type mice.

Fluorescence microcopy studies as well as quantitative measurements of ceramide revealed much higher concentrations of ceramide in CXCR2-deficient hepatocytes compared to wild-type controls (FIGS. 2A,B), consistent with a constitutive activation of neutral sphingomyelinase activity in CXCR2-deficient hepatocytes (FIG. 2C). Treatment of hepatocytes with the neutral sphingomyelinase inhibitor, GW4869, dose-dependently reduced the concentration of exosomes from CXCR2-deficient and wildtype hepatocytes (FIG. 2D). Collectively, this data indicates that neutral sphingomyelinase mediates the release of exosomes from hepatocytes. Deficiency of CXCR2 results in upregulation of neutral sphingomyelinase and ceramide levels and thereby promotes the release of exosomes from these cells.

Example 4

Exosomes Induce Hepatocyte Proliferation Via Sphingosine 1-phosphate

Figure 3:
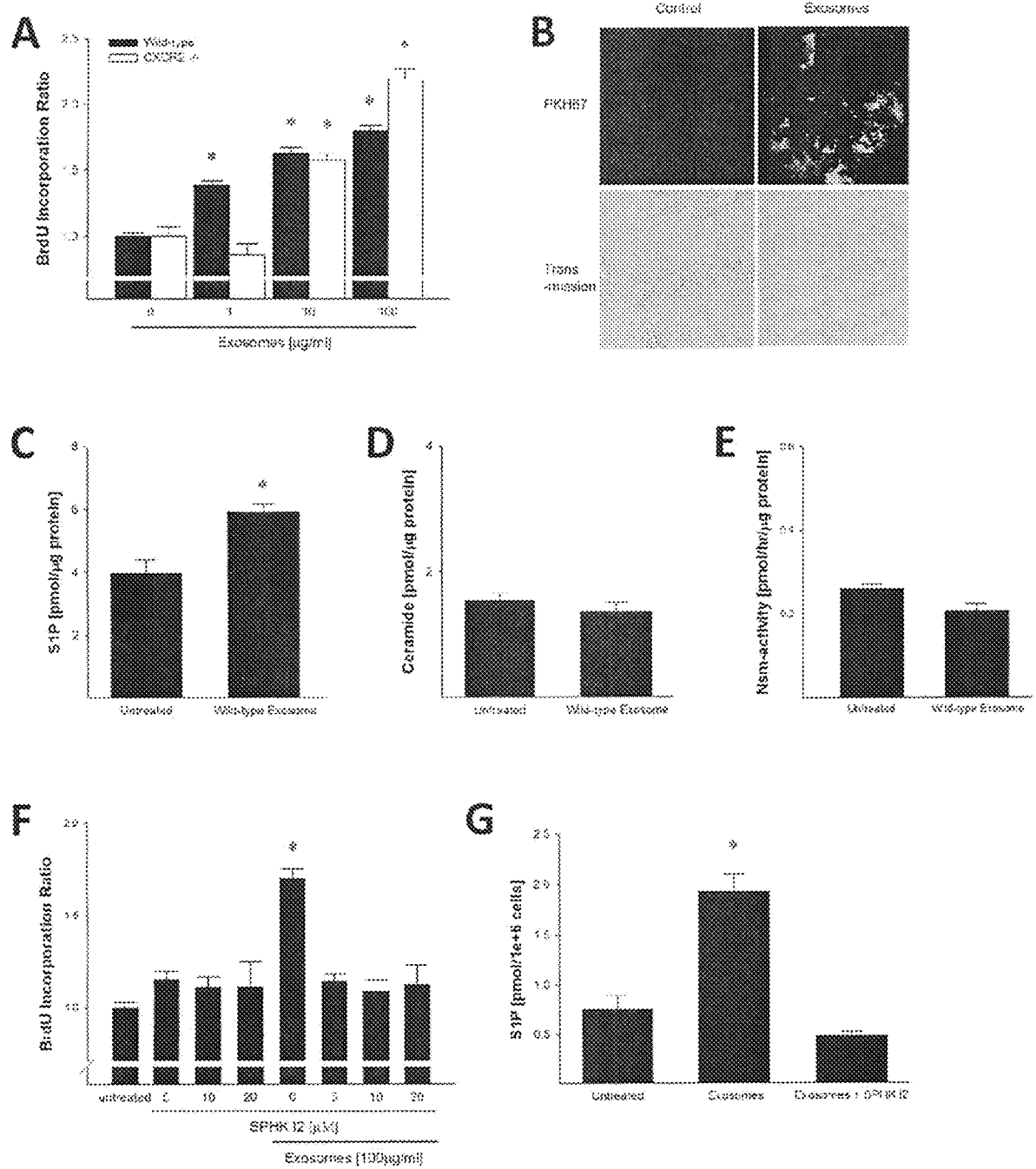
FIG. 3. Hepatocyte-derived exosomes dose-dependently induce hepatocyte proliferation by the induction of sphingosine-1-phosphate (S1P). (A) Primary mouse hepatocytes from wild-type mice were treated with increasing doses of exosomes derived from wild-type or CXCR2-deficient hepatocytes for 24 hrs. Cell proliferation was determined via BrdU incorporation. Data are mean±SEM with n=8-16 per group. *P<0.05 compared to control mice. **P<0.05 compared to untreated samples. (B) Hepatocyte-derived exosomes fuse with target hepatocytes and deliver their contents to the intracellular compartment. Hepatocyte exosomes were fluorescently labeled with the membrane marker PKH67 prior to addition to primary hepatocytes. Exosome components were incorporated into the plasma membrane as well as intracellular components, most likely endosomes. Exosomes induce sphingosine-1-phosphate (S1P) in hepatocytes as determined by ELISA (C), while they are without effect on ceramide concentration levels (D) and neutral sphingomyelinase activity (E). The induction of S1P in hepatocytes by exosomes was prevented by pre-incubation of hepatocytes with the sphingosine kinase inhibitor SPHK I2 (20 µM) (F). Inhibition of sphingosine kinase with 5-20 µM SPHK I2 completely abrogated exosome-induced proliferation of hepatocytes (G). Data are mean±SEM with n=3-4 per group. *P<0.05 compared to untreated mice.

Since exosomes are released from hepatocytes after I/R, whether these exosomes may have effects on hepatocyte proliferation was studied. To evaluate the effects of hepatocyte-derived exosomes on hepatocyte proliferation, DNA incorporation assays were conducted. Exosomes from wild-type hepatocytes increased hepatocyte proliferation in vitro (FIG. 3A), while exosomes from neutrophils were without effect (not shown). Further, to test whether exosomes derived from CXCR2-knockout hepatocytes were different from exosomes from wild-type hepatocytes, a dose-response curve with exosomes from wildtype and CXCR2-deficient mice was performed. The studies show a dose-dependent effect of exosomes on hepatocyte proliferation and higher doses of the exosomes doubled the proliferation rate of hepatocytes (FIG. 3A). However, the same number of exosomes from CXCR2-deficient hepatocytes had similar effects as those from wild-type cells (FIG. 3A) indicating that CXCR2 regulates the quantity, but not the proliferative capacity of exosomes.

To determine if treatment of hepatocytes with exosomes resulted in direct transfer of exosome components, hepatocytes were treated with exosomes that had been fluorescently labeled with PKH67, a cell membrane marker. Results show that exosome membranes are directly incorporated into the hepatocyte plasma membrane as well as the membranes of intracellular organelles—most likely endosomes (FIG. 3B). Based on these findings, it was hypothesized that sphingolipids contained within the exosome membranes trigger hepatocyte proliferation. Hepatoctyes that had been treated with exosomes had increased levels of sphingosine-1-phosphate (S1P), but no change in ceramide or neutral sphingomyelinase activity (FIG. 3C-E).

Because it was found that hepatocyte exosomes fuse with and are internalized by hepatocytes, that hepatocytes treated with exosomes had increased levels of S1P, and that studies in other cell types have shown that intracellular S1P can induce cell proliferation, whether exosome-induced hepatocyte proliferation was related to S1P levels was examined. Treatment of hepatocytes with SPHK I2, an inhibitor of sphingosine kinase, completely blocked exosome-induced production of S1P (FIG. 3F) and completely abrogated exosome-induced hepatocyte proliferation (FIG. 3G). These data suggest that exosomes induce hepatocyte proliferation via the generation of S1P in hepatocytes.

Example 5

Hepatocyte Exosomes Transfer their Own S1P Synthesis Machinery to Promote Hepatocyte Proliferation Next, whether exosomes carry S1P and/or the enzymes of the pathway mediating the synthesis of S1P as a cargo and, thereby, mediate the formation of S1P in hepatocytes, was examined. The results revealed that exosomes contain ceramide, neutral ceramidase, and sphingosine kinase, but not S1P or neutral sphingomyelinase (Table 1).

TABLE 1

Expression of S1P, Ceramide, Nsm-activity, Sphingosine kinase activity, Neutral ceramidase activity on hecatocyte-derived exosomes.

|  | exosomes |
|---|---|
| S1P [pmol/µg] | not detectable |
| Ceramide [pmol/µg] | 2.81 ± 0.97 |
| Nsm-activity [pmol/hr/µg] | not detectable |
| Sphingosine kinase activity [fmol/hr/µg] | 125.8 ± 43 |
| Neutral ceramidase activity [pmol/hr/µg] | 0.30 ± 0.08 |

Figure 4:
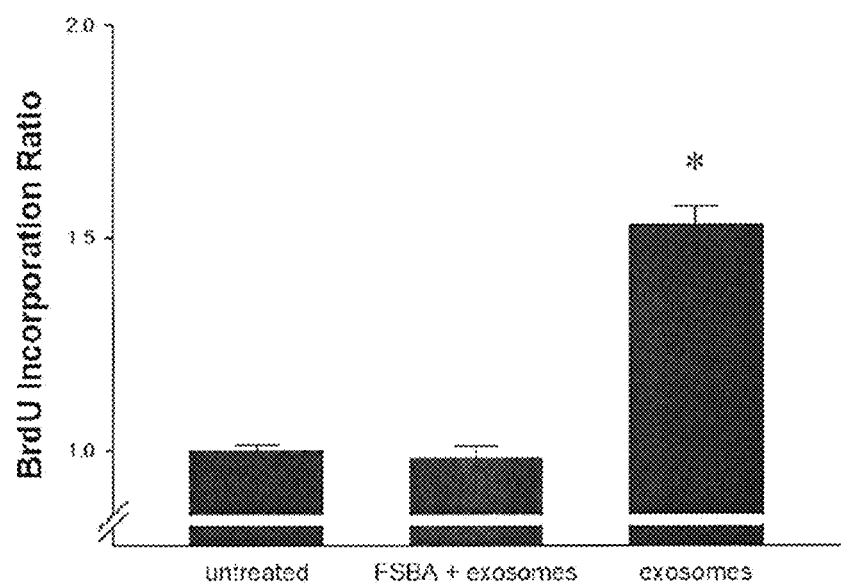
FIG. 4. Hepatocyte exosome sphingosine kinase mediates hepatocyte proliferation. FSBA is an irreversible inhibitor of sphingosine kinase that functions covalently blocking the ATP-binding. Exosomes were treated with FSBA or media control, thoroughly washed, then added to primary hepatocytes. Inhibition of sphingosine kinase with FSBA in exosomes completely blocked exosome-induced hepatocyte proliferation. Data are mean±SEM with n=4 per group. *P<0.05 compared to untreated samples.

This suggests that exosomes might transfer their own synthesis machinery to hepatocytes to synthesize S1P and thereby induce liver cell proliferation. To test this hypothesis and the role of exosomal vs. hepatocellular sphingosine kinase for the synthesis of S1P, the ATP binding site of sphingosine kinase present was covalently blocked in the exosomes by incubating exosomes with FSBA, an irreversible inhibitor of sphingosine kinase. This treatment completely blocked the proliferative effect of exosomes on hepatocytes (FIG. 4), proving that exosomes deliver sphingosine-kinase resulting in intracellular generation of S1P in hepatocytes leading to proliferation.

Example 6

Exosomes Induce Liver Regeneration In Vivo

Figure 5:
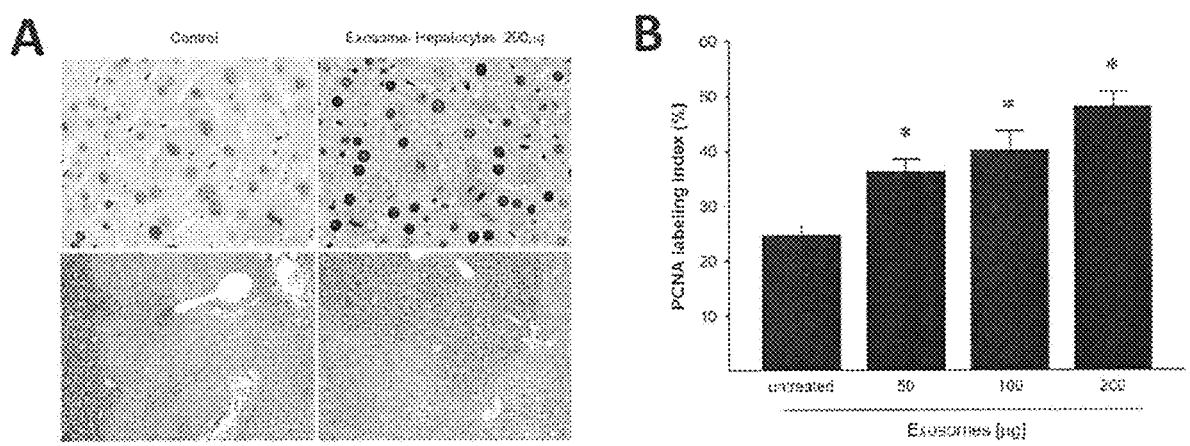
FIG. 5. Exosomes induce hepatocyte proliferation and liver regeneration after I/R in vivo. (A) Wild-type mice were injected intravenously with saline (control) or hepatocyte-derived exosomes 24 and 48 hours after I/R. Ischemic lobes were taken for histological analysis 72 hrs after reperfusion. Hepatocyte proliferation in ischemic liver was determined by immunohistochemical staining for proliferating cell nuclear antigen (PCNA; upper panel). Original magnification was 400×. Lower panel shows representative hematoxylin and eosin staining indicating much higher proliferation in livers of exosome-treated animals than in controls. (B) Quantitative analysis of PCNA labeling demonstrates a dose dependent effect of exosomes on liver cell proliferation in vivo. Data are mean±SEM with n=3-4 per group; *P<0.05 compared to untreated mice.

To assess whether exosomes induce liver regeneration in vivo, mice were treated with hepatocyte-derived exosomes and determined their effect on liver regeneration after I/R. Since liver regeneration after I/R is known to start 24 hrs after reperfusion, mice were injected intravenously with hepatocyte-derived exosomes 24 and 48 hrs after reperfusion. To mimic the in vivo effect of an increased exosome concentration in CXCR2-deficient mice after I/R, a detailed dose-response curve for the effects of exosomes on liver regeneration in vivo was performed. The results demonstrate a dose-dependent increase of hepatocyte proliferation (FIGS. 5a and b) suggesting that the increase of exosomes in CXCR2-deficient mice translates into an increased signal for liver regeneration in these mice.

While particular embodiments of the present invention have been illustrated and described, it would be obvious to one skilled in the art that various other changes and modifications can be made without departing from the spirit and scope of the invention. It is therefore intended to cover in the appended claims all such changes and modifications that are within the scope of this invention.

What is claimed is:

1. A method of inducing liver regeneration in a patient suffering from a liver injury associated with liver ischemia/reperfusion, the method comprising administering to the patient a therapeutic amount of exosomes formulated as an injectable suspension comprising a stable oil-in-water emulsion of lipid layer-encapsulated droplets, whereby liver regeneration is induced, and wherein a therapeutic amount is defined as an amount at least sufficient to result in a detectable increase in liver mass, wherein the exosomes are derived from a primary hepatocyte of a subject.

2. The method according to claim 1, wherein the exosomes are derived from a subject suffering from hepatic ischemia or reperfusion injury.

3. The method according to claim 1, wherein administering comprises intravenous administration or intra peritoneal administration.

4. A method of inducing liver regeneration in a patient suffering from a liver injury associated with liver ischemia/reperfusion, the method comprising administering to the patient a therapeutic amount of a pharmaceutical composition comprising sphingosine kinase 2, and, optionally, ceramide and ceramidase, contained in a lipid delivery system, whereby liver regeneration is induced, and wherein a therapeutic amount is defined as an amount at least sufficient to result in a detectable increase in liver mass.

5. A method of up-regulating synthesis of sphingosine-1-phosphate (S1P) in a hepatocyte, the method comprising contacting the hepatocyte with at least one vesicle having a surface lipid layer conjugated with hepatocyte target antigen, said vesicle encapsulating sphingosine kinase 2, ceramide and neutral ceramidase.

6. The method according to claim 4, wherein the composition comprises sphingosine kinase 2, ceramide and ceramidase.

7. The method according to claim 4, wherein the lipid delivery system comprises a stable oil-in-water emulsion of lipid layer-encapsulated droplets.

8. The method according to claim 7, wherein a hepatocyte target antigen is conjugated to a surface of the lipid layer.

9. The method according to claim 4, wherein the step of administering comprises intravenous or intra peritoneal administration.

10. The method according to claim 1, wherein the lipid layer comprises a plurality of hepatocyte target antigen conjugated to an outer surface of the lipid layer.

* * * * *